United States Patent

Krapcho et al.

[11] 3,962,222
[45] June 8, 1976

[54] 3a,4,6,7-TETRAHYDRO-3-PHENYL-7-(PHENYLALKYLENE)-THIOPYRANO[4,3-c]PYRAZOLE-2(3H)-ALKANAMINE, AND ANALOGS

[75] Inventors: John Krapcho, Somerset; Chester F. Turk, Kendall Park; George C. Rovnyak, Hopewell, all of N.J.

[73] Assignee: E. R. Squibb & Sons, Inc., Princeton, N.J.

[22] Filed: Aug. 1, 1975

[21] Appl. No.: 600,998

[52] U.S. Cl.................. 260/240 F; 260/310 C; 424/273; 424/275
[51] Int. Cl.².................................... C07D 495/06
[58] Field of Search................. 260/310 C, 240 F

[56] References Cited
UNITED STATES PATENTS
3,897,420   7/1975   Krapcho et al.................. 260/240 F Primary Examiner—Allen B. Curtis
Attorney, Agent, or Firm—Lawrence S. Levinson; Merle J. Smith; Donald J. Barrack

[57] ABSTRACT

Anti-inflammatory activity and hypotensive activity are exhibited by compounds having the formula

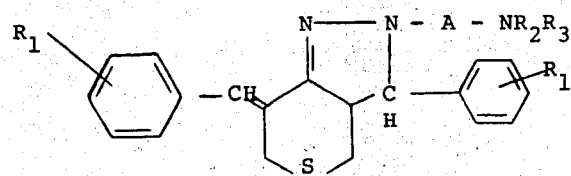

the salts thereof, and the 5-oxide and 5,5-dioxide thereof, wherein A is a straight or branched chain alkylene group; $R_1$ is hydrogen, alkyl, alkoxy, trifluoromethyl, or halogen; $R_2$ is hydrogen or alkyl; and $R_3$ is hydrogen, alkyl, phenyl, or phenylalkyl.

11 Claims, No Drawings

3A,4,6,7-TETRAHYDRO-3-PHENYL-7-(PHENYLALKYLENE)-THIOPYRANO[4,3-C]PYRAZOLE-2(3H)-ALKANAMINE, AND ANALOGS

BRIEF DESCRIPTION OF THE INVENTION

Compounds having the formula

I

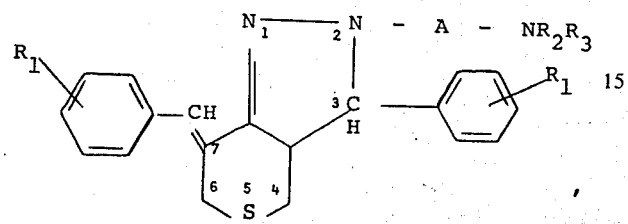

the 5-oxide and 5,5-dioxide thereof, and the pharmaceutically acceptable acid addition and quaternary ammonium salts thereof, have useful pharmacological activities, and can be used in mammals to treat inflammation and to lower blood pressure. In formula I, and throughout the specification, the symbols are as defined below.

A can be a straight or branched chain alkylene group having 2 to 5 carbon atoms;

$R_1$ can be hydrogen, alkyl, alkoxy, trifluoromethyl, or halogen;

$R_2$ can be hydrogen or alkyl; and $R_3$ can be hydrogen, alkyl, phenyl, or phenylalkyl.

The terms alkyl and alkoxy, as used throughout the specification, refer to groups having 1 to 8 carbon atoms. Alkyl and alkoxy groups having 1 to 3 carbon atoms are preferred.

The term phenylalkyl, as used throughout the specification, refers to groups of the formula

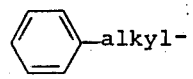

wherein alkyl is as defined above. Benzyl and phenethyl are the preferred phenylalkyl groups.

The term halogen, as used throughout the specification, refers to fluorine, chlorine, bromine, and iodine; fluorine and chlorine are preferred.

DETAILED DESCRIPTION OF THE INVENTION

The compounds of formula I (and the 5-oxides and 5,5-dioxides thereof) are prepared using as starting materials a substituted tetrahydro-4H-thiopyran-4-one having the formula

II

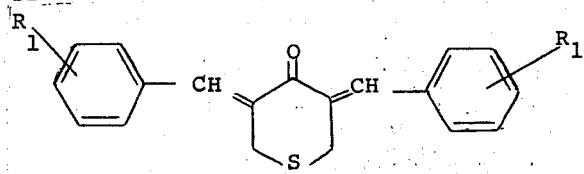

or a 1-oxide or 1,1-dioxide thereof, and a hydrazine having the formula

III $H_2NNH—A—NR_2R_3$.

The compounds of formulas II and III are readily obtainable; see, for example, *Journal of the American Chemical Society*, 79:156 (1957) and *Journal of Medicinal Chemistry*, 7:493 (1964).

A substituted tetrahydro-4H-thiopyran-4-one of formula II can be prepared by reacting tetrahydro-4H-thiopyran-4-one with an appropriate benzaldehyde having the formula IV 

The corresponding 1-oxide or 1,1-dioxide can be prepared by reacting a substituted tetrahydro-4H-thiopyran-4-one of formula II with an appropriate amount of an oxidizing agent; sodium periodate is preferred for preparing a 1-oxide and hydrogen peroxide is preferred for preparing a 1,1-dioxide.

A hydrazine of formula III can be prepared by reacting an excess of hydrazine ($H_2NNH_2$) with a haloamine having the formula

V $X—A—NR_2R_3$, wherein X is chlorine or bromine.

Reaction of a substituted tetrahydro-4H-thiopyran-4-one of formula II (or a 1-oxide or 1,1-dioxide thereof) with a hydrazine of formula V yields a product of formula I, or the corresponding 5-oxide or 5,5-dioxide. The reaction can be run in an organic solvent, preferably a lower alkanol such as methanol. While reaction conditions are not critical, the reaction will preferably be run at, or near, the reflux temperature of the solvent.

Alternatively, the compounds of formula I can be obtained by first reacting a substituted tetrahydro-4H-thiopyran-4-one of formula II with a hydroxyalkyl hydrazine having the formula

VI $H_2NNH—A—OH$ to form an intermediate having the formula

VII

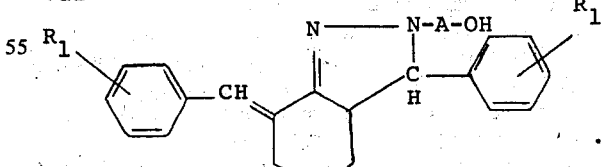

An alcohol of formula VII can be reacted with an alkylsulfonyl or arylsulfonyl halide, preferably p-toluenesulfonyl halide, to yield a compound of the formula

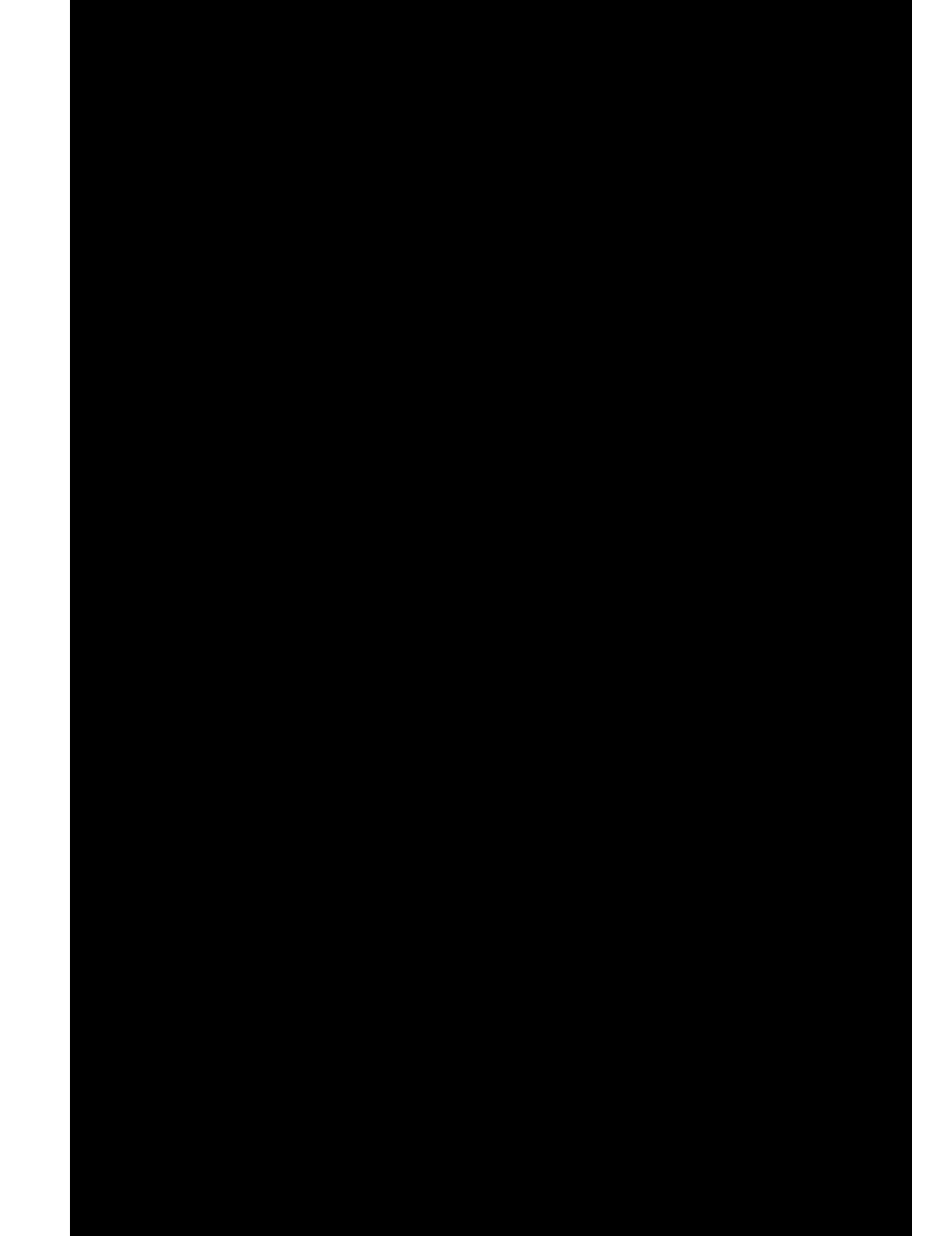

A solution of 10.4g of sodium periodate in 50ml of water is added to a suspension of 7.0g of tetrahydro-3,5-bis-(phenylmethylene)-4H-thiopyran-4-one in 300ml of methanol. The mixture is stirred at room temperature for 3 days (a water bath is used for the first hour to moderate a slightly exothermic reaction). Solvent is removed in vacuo and the residue is stirred with chloroform and filtered. The filtrate is concentrated in vacuo and the residue is crystallized from 150ml of methanol, giving 6.4g of the title compound, melting point 155°–160°C. A second crop of 0.5g of the title compound, melting point 154°–157°C is also obtained.

B. 3a,4,6,7-Tetrahydro-N,N-dimethyl-3-phenyl-7-(phenylmethylene)thiopyrano[4,3-c]pyrazole-2-(3H)-propanamine, 5-oxide (two isomers)

A stirred mixture of 2.5g of tetrahydro-3,5-bis-(phenylmethylene)-4H-thiopyran-4-one, 1-oxide and 0.95g of 3-dimethylaminopropylhydrazine in 75ml of methanol is heated and the resulting solution is refluxed for 5 hours. After standing overnight at room temperature, the methanol is removed on a rotary evaporator and the residue is triturated with 100ml of boiling isopropyl ether to yield a solid, which after cooling weighs 2.0g, melting point 138°–140°C.

Thin layer chromatography (ethyl acetate on alumina) shows a mixture of compounds is present. Crystallization from 10ml of acetonitrile yields 0.9g of material, melting point 153°–155°C. (TLC: single spot; ethyl acetate on alumina $R_f$ 0.38). The acetonitrile liquor is evaporated and the residue is dissolved in 4ml of acetonitrile. Cooling overnight yields 0.15g of material, melting point 125°–127°C (TLC: essentially single spot; ethyl acetate on alumina, $R_f$ 0.31; small amount of material with $R_f$ 0.38 present).

EXAMPLE 4

3a,4,6,7-Tetrahydro-N,N-dimethyl-3-phenyl-7-(phenylmethylene)thiopyrano[4,3-c]pyrazole-2(3H)-propanamine-5,5-dioxide Tetrahydro-3,5-bis-(phenylmethylene)-4H-thiopyran-4-one, 1,1-dioxide (4.9g, prepared as described in *Journal of American Chemical Society*, 79:156 (1957)) is reacted with 1.8g of 3-dimethylaminopropylhydrazine in 200 ml of methanol for 4 hours. The solvent is evaporated off and the residue is extracted with 400ml of boiling isopropyl ether, leaving 2.3g of material undissolved. The extract is filtered through glass wool and concentrated to 150ml; the title compound separates. After cooling for 72 hours, the material is filtered, washed with isopropyl ether and dried in vacuo to yield 3.5g of the title compound, melting point 127°–129°C.

EXAMPLE 5

3a,4,6,7-Tetrahydro-N,N-dimethyl-3-phenyl-7-(phenylmethylene)thiopyrano[4,3-c]pyrazole-2(3H)-propanamine-5,5-dioxide, hydrochloride (1:1)

3a,4,6,7-Tetrahydro-N,N-dimethyl-3-phenyl-7-(phenylmethylene)thiopyrano[4,3-c]pyrazole-2(3H)-propanamine-5,5-dioxide (3.4g) is dissolved in 25ml of warm methyl ethyl ketone, cooled and treated with 1.35ml of 6.1N alcoholic hydrogen chloride. On seeding and rubbing, the crystalline hydrogen chloride salt separates. Ether is added to complete the precipitation and after cooling for about 16 hours the solid is filtered, washed with ether and dried in vacuo to give 3.5g of material, melting point 183°–185°C. Following crystallization from 20ml of methanol-40ml of ether, there remains 2.6g of the title compound, melting point 192°–194°C.

EXAMPLE 6

3a,4,6,7-Tetrahydro-3-phenyl-7-(phenylmethylene)-thiopyrano[4,3-c]pyrazole-2(3H)-ethanamine A. 3a,4,6,7-Tetrahydro-3-phenyl-7-(phenylmethylene)thiopyrano[4,3-c]pyrazole-2(3H)-ethanol Following the procedure of Example 1, but substituting (2-hydroxyethyl)hydrazine for 3-dimethylaminopropylhydrazine, yields the title compound.

B. 3a,4,6,7-Tetrahydro-3-phenyl-7-(phenylmethylene)thiopyrano[4,3-c]pyrazole-2(3H)-ethanamine 3a,4,6,7-Tetrahydro-3-phenyl-7-(phenylmethylene)-thiopyrano[4,3-c]pyrazole-2(3H)-ethanol is suspended in pyridine and treated with one equivalent of tosyl chloride. After standing at room temperature for about 16 hours, the mixture is poured into water and the tosylate is dissolved in ethanol, cooled and saturated with ammonia gas. After standing for 3 days, the excess ammonia and solvent are removed by evaporation to give the title compound.

EXAMPLE 7

3a,4,6,7-Tetrahydro-N,N-dimethyl-3-phenyl-7-(phenylmethylene)thiopyrano[4,3-c]pyrazole-2(3H)-propanamine, methochloride A solution of 3.0g of 3a,4,6,7-tetrahydro-N,N-dimethyl-3-phenyl-7-(phenylmethylene)thiopyrano[4,3-c]pyrazole-2(3H)-propanamine (from Example 1) in 30ml in acetonitrile is cooled and treated with 5.0g of methyl chloride gas. The resulting solution is allowed to stand at room temperature for a day and the solvent is evaporated to give the title compound.

EXAMPLES 8–14

Following the procedure of Example 1, but substituting the compound listed in column I for tetrahydro-3,5-bis-(phenylmethylene)-4H-thiopyran-4-one and the compound listed in column II for 3-dimethylaminopropylhydrazine, yields the compound listed in column III.

| Example | Column I | Column II | Column III |
|---|---|---|---|
| 8 | tetrahydro-3,5-bis-[(2-methylphenyl)methylene]-4H-thiopyran-4-one | methylaminopropylhydrazine | 3a,4,6,7-tetrahydro-N-methyl-3-(2-methylphenyl)-7-[(2-methylphenyl)methylene]thiopyrano[4,3-c]pyrazole-2(3H)-propanamine |
| 9 | tetrahydro-3,5-bis-[(4-methoxyphenyl)methylene]4H-thiopyran-4-one | N-benzyl-N-methylaminoethylhydrazine | 3a,4,6,7-tetrahydro-N-benzyl-N-methyl-3-(4-methoxyphenyl)-7-[(4-methoxyphenyl)methylene]thio- |

| Example | Column I | Column II | Column III |
|---|---|---|---|
| | | | pyrano[4,3-c]pyrazole-2-(3H)-ethanamine |
| 10 | tetrahydro-3,5-bis-[(4-trifluoromethylphenyl)methylene]-4H-thiopyran-4-one | N-methyl-N-phenylaminopentylhydrazine | 3a,4,6,7-tetrahydro-N-methyl-N-phenyl-3-(4-trifluoromethylphenyl)-7-[(4-trifluoromethylphenyl)methylene]thiopyrano[4,3-c]pyrazole-2(3H)-pentanamine |
| 11 | tetrahydro-3,5-bis-[(2-chlorophenyl)methylene]-4H-thiopyran-4-one | (2-aminoethyl)hydrazine | 3a,4,6,7-tetrahydro-3-(2-chlorophenyl)-7-[2-(chlorophenyl)methylene]-thiopyrano[4,3-c]pyrazole-2(3H)-ethanamine |
| 12 | tetrahydro-3,5-bis-(phenylmethylene)-4H-thiopyran-4-one | phenylaminopropylhydrazine | 3a,4,6,7-tetrahydro-N-phenyl-3-phenyl-7-(phenylmethylene)thiopyrano[4,3-c]-pyrazole-2(3H)-propanamine |
| 13 | tetrahydro-3,5-bis-(phenylmethylene)-4H-thiopyran-4-one | benzylaminopropylhydrazine | 3a,4,6,7-tetrahydro-N-benzyl-3-phenyl-7-(phenylmethylene)thiopyrano[4,3-c]-pyrazole-2(3H)-propanamine |
| 14 | tetrahydro-3,5-bis-[(4-propoxyphenyl)methylene]-4H-thiopyran-4-one | 3-(dimethylamino)-2-methylpropylhydrazine | 3a,4,6,7-tetrahydro-N,N,β-trimethyl-3-(4-propoxyphenyl)-7-[(4-propoxyphenyl)-methylene]thiopyrano[4,3-c]pyrazole-2(3H)-propanamine. |

What is claimed is:
1. A compound having the formula

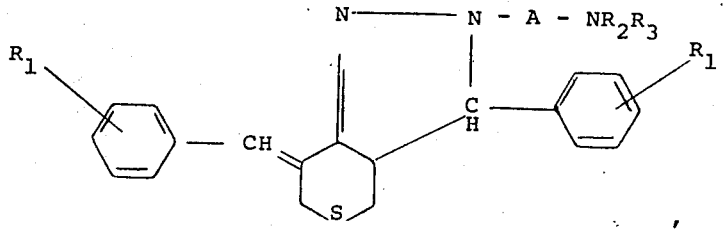

a pharmaceutically acceptable acid addition salt thereof, a quaternary ammonium salt thereof, or a 5-oxide or 5,5-dioxide thereof, wherein A is a straight or branched chain alkylene group having 2 to 5 carbon atoms; $R_1$ is hydrogen, alkyl, alkoxy, trifluoromethyl, or halogen; $R_2$ is hydrogen or alkyl; and $R_3$ is hydrogen, alkyl, phenyl, or phenylalkyl; wherein alkyl and alkoxy refer to groups having 1 to 8 carbon atoms.

3. A compound in accordance with claim 1 wherein A is —$CH_2$—$CH_2$—$CH_2$—.

4. A compound in accordance with claim 1 wherein $R_1$ is hydrogen.

5. A compound in accordance with claim 1 wherein $R_1$ is hydrogen and $R_3$ is alkyl.

6. A compound in accordance with claim 1 wherein $R_2$ and $R_3$ are both alkyl.

7. The compound in accordance with claim 1 having the name 3a,4,6,7-tetrahydro-N,N-dimethyl-3-phenyl-7-(phenylmethylene)thiopyrano[4,3-c]pyrazole-2(3H)-propanamine.

2. A compound in accordance with claim 1 wherein A is —$CH_2$—$CH_2$— or —$CH_2$—$CH_2$—$CH_2$—.

8. The compound in accordance with claim 1 having the name 3a,4,6,7-tetrahydro-N,N-dimethyl-3-phenyl-7-(phenylmethylene)thiopyrano[4,3-c]pyrazole-2(3H)-propanamine, maleate.

9. The compound in accordance with claim 1 having the name 3a,4,6,7-tetrahydro-N,N-dimethyl-3-phenyl-7-(phenylmethylene)thiopyrano[4,3-c]pyrazole-2(3H)-propanamine-5-oxide.

10. The compound in accordance with claim 1 having the name 3a,4,6,7-tetrahydro-N,N-dimethyl-3-phenyl-7-(phenylmethylene)thiopyrano[4,3-c]pyrazole-2(3H)-propanamine-5,5-dioxide.

11. The compound in accordance with claim 1 having the name 3a,4,6,7-tetrahydro-N,N-dimethyl-3-phenyl-7-(phenylmethylene)thiopyrano[4,3-c]pyrazole-2(3H)-propanamine-5,5-dioxide, hydrochloride.

\* \* \* \* \*